United States Patent [19]

Dreikorn

[11] 4,001,227
[45] Jan. 4, 1977

[54] TETRAZOLO- AND TRIAZOLOBENZOTHIAZINES

[75] Inventor: Barry A. Dreikorn, Indianapolis, Ind.
[73] Assignee: Eli Lilly and Company, Indianapolis, Ind.
[22] Filed: Dec. 22, 1975
[21] Appl. No.: 643,273
[52] U.S. Cl. .................. 260/243 R; 424/246
[51] Int. Cl.² ........................ C07D 279/08
[58] Field of Search ................ 260/243 R

[56] References Cited
UNITED STATES PATENTS

| | | | |
|---|---|---|---|
| 3,389,137 | 6/1968 | Mosby | 260/256.4 |
| 3,764,681 | 10/1973 | Dreikorn | 424/258 |
| 3,839,569 | 10/1974 | Dreikorn et al. | 424/258 |
| 3,929,783 | 12/1975 | Krapcho et al. | 260/243 R |

FOREIGN PATENTS OR APPLICATIONS

| | | |
|---|---|---|
| 803,098 | 12/1973 | Belgium |
| 2,249,350 | 4/1974 | Germany |

*Primary Examiner*—John M. Ford
*Attorney, Agent, or Firm*—Joseph A. Jones; Everet F. Smith

[57] ABSTRACT

A class of 5H-tetrazolo[1,5-a][3,1]benzothiazines and 5H-s-triazolo[4,3-a][3,1]benzothiazines are fungicides useful for the protection of plants from fungal foliar phytopathogens.

6 Claims, No Drawings

TETRAZOLO- AND TRIAZOLOBENZOTHIAZINES

BACKGROUND OF THE INVENTION

This invention belongs to the art of agricultural chemistry, and provides new compounds useful for protecting plants from, and reducing the adverse effects of, fungal foliar phytopathogens. The protection of plants from such phytopathogens is of great importance, since nearly every ornamental and crop plant is injured by disease caused by them. Many important crops cannot be economically grown without chemically protecting the plant from such phytopathogens.

Some prior publications are important to an understanding of the background of this invention. Dreikorn, U.S. Pat. Nos. 3,764,681 and 3,839,569, disclosed the fungicidal efficacy of tetrazolo[1,5-a]quinolines and s-triazolo[4,3-a]quinolines. Further fungicidal multiple-fused-ring compounds are disclosed by such publications as Belgian Pat. No. 803,098 and West German Offenlegungsschrift No. 2,249,350.

SUMMARY OF THE INVENTION

This invention provides new compounds of the formula

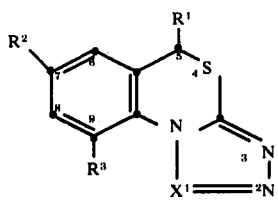

wherein X represents

R represents hydrogen or $C_1$–$C_4$ alkyl;
$R^1$ represents hydrogen or phenyl;
$R^2$ and $R^3$ independently represent hydrogen, $C_1$–$C_3$ alkyl, chloro or bromo;
provided that at least one of $R^2$ and $R^3$ represents hydrogen; that $R^3$ represents hydrogen when X represents

and R represents $C_1$–$C_4$ alkyl; and that $R^2$ does not represent $C_1$–$C_3$ alkyl when X represents

A preferred class of compounds includes those wherein X represents

and $R^1$ represents hydrogen.

The invention also provides methods for the control of fungal foliar phytopathogens using the compounds.

DESCRIPTION OF THE PREFERRED EMBODIMENT

In the above formula, the terms $C_1$–$C_3$ alkyl and $C_1$–$C_4$ alkyl refer to such groups as methyl, ethyl, propyl, isopropyl, butyl, and t-butyl.

The typical compounds below are presented to help the reader to understand the invention, but do not, of course, represent the bounds of it.

7-chloro-5H-tetrazolo[1,5-a][3,1]benzothiazine
9-isopropyl-5H-tetrazolo[1,5-a][3,1]benzothiazine
9-ethyl-5-phenyl-5H-tetrazolo[1,5-a][3,1]benzothiazine
7-bromo-5H-tetrazolo-8 1,5-a][3,1]benzothiazine
9-bromo-5H-tetrazolo[1,5-a][3,1]benzothiazine
7-chloro-5-phenyl-5H-tetrazolo[1,5-a][3.1]benzothiazine
9-methyl-5-phenyl-5H-tetrazolo[1,5-a][3,1]benzothiazine
7-bromo-5-phenyl-5H-tetrazolo[1,5-a][3.1]benzothiazine
5-phenyl-5H-s-triazolo[4,3-a][3,1]benzothiazine
9-propyl-5H-s-triazolo[4,3-a][3,1]benzothiazine
1-butyl-5-phenyl-5H-s-triazolo[4,3-a][3,1]benzothiazine
7-bromo-1-methyl-5H-s-triazolo[4,3-a][3,1]benzothiazine
9-chloro-5-phenyl-5H-s-triazolo[4,3-a][3,1]benzothiazine
1-ethyl-7-methyl-5-phenyl-5H-s-triazolo[4,3-a]-[3,1]benzothiazine
7-isopropyl-5H-s-triazolo[4,3-a][3,1]benzothiazine
7-ethyl-1-propyl-5H-s-triazolo[4,3-a][3,1]benzothiazine
1-(s-butyl)-5H-s-triazolo[4,3-a][3,1]benzothiazine
7-methyl-5-phenyl-1-propyl-5H-s-triazolo[4,3-a][3,1]benzothiazine
1-(t-butyl)- 7-chloro-5H-s-triazolo[4,3-a][3,1]-benzothiazine
9-chloro-5-phenyl-5H-tetrazolo[1,5-a][3,1]benzothiazine
9-bromo-5-phenyl-5H-s-triazolo[4,3-a][3,1]benzothiazine
9-ethyl-5-phenyl-5H-s-triazolo[4,3-a][3,1]benzothiazine
5-phenyl-5H-tetrazolo[1,5-a][3,1]benzothiazine The preferred compounds are 9-chloro-5H-tetrazolo[1,5-a][3,1]benzothiazine, 5H-tetrazolo[1,5-a][3,1]benzothiazine, 9-methyl-5-H-s-triazolo[4,3-a][3,1]benzothiazine, 1,7-dimethyl-5H-s-triazolo[4,3-a][3,1]benzothiazine, 9-chloro-5H-s-triazolo[4,3-a][3,1]benzothiazine, 9-methyl-5H-tetrazolo[1,5-a][3,1]benzothiazine, 7-chloro-1-methyl-5-phenyl-5H-s-triazolo[4,3-a][3,1]benzothiazine and 1-methyl-5H-s-triazolo[4,3-a][3,1]benzothiazine.

The compounds are made by various processes, all of which start from an appropriately substituted 1,4-dihydro-2H-3,1-benzothiazin-2-thione. The starting compounds are readily made, as taught by Kitamura, J. Pharm. Soc. Japan 57, 54–57 (1937), from the corresponding 2-aminobenzyl alcohols by reaction with carbon disulfide in the presence of a strong base, preferably potassium hydroxide, in a lower alkanol at temperature from 25° C. to 80° C. Example 1 below exemplifies the preparation of a typical thione starting compound.

The tetrazoles of this invention are preferably made by reacting the thione starting compound with phosphorous oxychloride to form the 2-chlorobenzothiazine, which is then cyclized to form the tetrazolobenzothiazine by reaction with azide ion. The reaction with phosphorus oxychloride is done neat, or in a halogenated solvent such as chloroform, methylene chloride or the like, or in an aromatic solvent such as benzene or xylene. Reaction temperatures from 25° C. to 100° C. can be used; the reflux temperature of the reaction mixture is preferred.

Reaction of the chlorobenzothiazine with azide ion is preferably carried out at a low temperature in the range of −25° C. to 0° C. in the presence of a solvent such as dimethylformamide or tetrahydrofuran. Azide ion is preferably provided in the form of sodium azide, but other sources, such as potassium azide and even lower alkyl azides, may also be used.

The tetrazoles may also be synthesized by first converting the thione to the corresponding ketone with an oxidizing agent, preferably hydrogen peroxide in the presence of a strong base such as potassium hydroxide or sodium carbonate. The ketone is then converted to the chloro compound and cyclized as described above.

The tetrazoles may also be prepared by first reacting the thione starting compounds with hydrazine in any convenient inert solvent, such as a lower alkanol, at a temperature from about 0° C. to about 50° C. and reacting the hydrazine derivatives so formed with nitrite ion in the presence of an alkanoic acid. Sodium or potassium nitrite are the preferred sources of nitrite ion, and acetic acid at a temperature from about −5° C. to about 25° C. is the preferred reaction medium.

The triazoles of this invention are prepared by first reacting the thione with hydrazine as described above. The thiazole ring is then closed by reaction of the hydrazino intermediate with a $C_1$–$C_4$ alkanoic acid. When formic acid is used, the product is the compound wherein R represents hydrogen; acetic acid provides a methyl R substituent, and so forth. The cyclization proceeds in good yields at temperatures from about 50° C. to about 100° C., preferably at the reflux temperature of the reaction mixture. The reaction is preferably carried out without solvent, but aromatic solvents such as benzene and xylene, halogenated solvents such as chloroform and methylene chloride, and alkanol solvent may be used if desired in a particular reaction.

The following specific preparation examples are typical of the synthetic methods used to prepare all of the compounds of this invention. The products of the examples were identified by nuclear magnetic resonance analysis, elemental microanalysis, and, in some cases, by mass spectrometry.

EXAMPLE 1

8-chloro-1,4-dihydro-2H-3,1-benzothiazin-2-thione

A 9 g. portion of 2-amino-3-chlorobenzyl alcohol was combined with 15 ml. of carbon disulfide and 5 g. of potassium hydroxide in 100 ml. of ethanol. The reaction mixture was stirred at reflux temperature overnight, and was then dumped into ice. After the aqueous mixture was acidified with hydrochloric acid, the product was extracted from the mixture with methylene chloride and was purified by chromatography over alumina with chloroform-hexane as the eluent. After recrystallization from methanol, 3,2 g. of 8-chloro-1,4-dihydro-2H-3,1-benzothiazin-2-thione, m.p. 125°–126° C., was obtained.

EXAMPLE 2

9-chloro-5H-tetrazolo[1,5-a][3,1]benzothiazine

The intermediate product made in Example 1 was added to 75 ml. of phosphorus oxychloride and the mixture was stirred at reflux temperature for 4 hours. The excess phosphorus oxychloride was then evaporated under vacuum, and the residue was taken up in 100 ml. of tetrahydrofuran and added to a suspension of 5 g. of sodium azide in 25 ml. of dimethylformamide at 0° C. After stirring overnight at constant temperature, the mixture was poured into water, and the product was recovered by filtration and recrystallized from ethanol to produce 0.83 g. of 9-chloro-5H-tetrazolo[1,5-a][3,1]benzothiazine, m.p. 164° C. dec.

|   | Theoretical | Found |
| --- | --- | --- |
| C | 42.77% | 43.03% |
| H | 2.24 | 2.35 |
| N | 24.94 | 24.91 |

EXAMPLE 3

9-methyl-5H-tetrazolo[1,5-a][3,1]benzothiazine

The process of Example 2 was followed, starting with 4 g. of 1,4-dihydro-8-methyl-2H-3,1-benzothiazin-2-thione, to prepare 0.45 g. of 9-methyl-5H-tetrazolo[1,5-a][3,1]benzothiazine, m.p. 174° C.

|   | Theoretical | Found |
| --- | --- | --- |
| C | 52.92% | 52.63% |
| H | 3.95 | 4.15 |
| N | 27.43 | 27.22 |

EXAMPLE 4

5H-tetrazolo[1,5-a][3,1]benzothiazine

A 5 g. portion of 1,4-dihydro-2H-3,1-benzothiazin-2-thione was dissolved in 800 ml. of denatured ethanol, and 15 ml. of hydrazine was added. After the reaction mixture was stirred at room temperature for 3 hours, 10 ml. of glacial acetic acid was added and the solvent was removed under vacuum. The remaining oil was dissolved in 20 ml. of additional acetic acid, cooled to −5° C., and 10 ml. of saturated sodium nitrite solution was added slowly while the temperature of the mixture was held below 0° C. After the addition was complete, the mixture was poured into water with the formation of a white precipitate of product, which was collected by filtration and recrystallized from methanol. The yield was 1.15 g. of 5H-tetrazolo[1,5-a][3,1]benzothiazine, m.p. 137° C.

|   | Theoretical | Found |
| --- | --- | --- |
| C | 50.51% | 50.28% |
| H | 3.18 | 3.45 |
| N | 29.45 | 29.69 |
| S | 16.86 | 16.64 |

EXAMPLE 5

5H-s-triazolo[4,3-a][3,1]benzothiazine

Five g. of 1,4-dihydro-2H-3,1-benzothiazin-2-thione was dissolved in 400 ml. of denatured ethanol, and 15 ml. of anhydrous hydrazine was added. The mixture was stirred at room temperature for about 2½ hours, after which 50 ml. of formic acid was added. The mixture was then stirred overnight, and was evaporated to dryness under vacuum. Fifty ml. of additional formic acid was then added, and the mixture was stirred at reflux temperature for 20 hours. Excess formic acid was then removed under vacuum, and the residue was dissolved in methylene chloride. The solution was washed successively with water, saturated sodium bicarbonate solution, and water. The organic solution was then dried over sodium sulfate and evaporated to dryness. The remaining solid product was recrystallized from methanol to produce 1.2 g. of 5H-s-triazolo[4,3-a]-[3,1]benzothiazine, m.p. 188°–190° C.

|   | Theoretical | Found |
|---|---|---|
| C | 57.12% | 57.37% |
| H | 3.73 | 3.82 |
| N | 22.21 | 21.97 |
| S | 16.94 | 16.65 |

EXAMPLE 6

1-ethyl-5H-s-triazolo[4,3-a][3,1benzothiazine

The general process of Example 5 was followed, starting with 3.6 g. of the same benzothiazin-2-thione and using propionic acid instead of formic acid in the last step. Chromatography over silica gel, with ethyl acetate as eluent, was used to purify the product. The yield was 1.6 g. of 1-ethyl-5H-s-triazolo[4,3-a][3,1]benzothiazine, m.p. 131°–132° C.

|   | Theoretical | Found |
|---|---|---|
| C | 60.83% | 60.68% |
| H | 5.07 | 4.88 |
| N | 19.35 | 19.10 |

EXAMPLE 7

1-methyl-5H-s-triazolo[4,3-a][3,1]benzothiazine

The general process of Example 5 was followed again, starting with 5 g. of the same starting compound, and using acetic acid in the final step of the synthesis. The yield was 1.21 g. of 1-methyl-5H-s-triazolo[4,3-a][3,1]-benzothiazine, m.p. 142°–144° C.

|   | Theoretical | Found |
|---|---|---|
| C | 59.09% | 58.89% |
| H | 4.46 | 4.17 |
| N | 20.67 | 20.88 |
| S | 15.77 | 15.96 |

EXAMPLE 8

1-propyl-5H-s-triazolo[4,3-a][3,1]benzothiazine

The process of Example 5 was followed again, starting with 3.6 g. of the starting compound and using butyric acid in place of formic acid in the cyclization step. The hydrazine reaction was run at 0° C. The product, which was purified by chromatography as done in Example 6, and 0.8 g. of 1-propyl-5H-s-triazolo[4,3-a][3,1]benzothiazine, m.p. 114° C.

|   | Theoretical | Found |
|---|---|---|
| C | 62.31% | 62.21% |
| H | 5.66 | 5.62 |
| N | 18.17 | 18.10 |

EXAMPLE 9

9-methyl-5H-s-triazolo[4,3-a][3,1]benzothiazine

A 4 g. portion of 1,4-dihydro-8-methyl-2H-3,1-benzothiazin-2-thione was the starting compound for a process essentially similar to that of Example 5, except that the hydrazine reaction was run at 0° C. The product was 1 g. of 9-methyl-5H-s-triazolo[4,3-a][3,1]benzothiazine, m.p. 234° C.

|   | Theoretical | Found |
|---|---|---|
| C | 59.09% | 58.86% |
| H | 4.46 | 4.60 |
| N | 20.67 | 20.46 |

EXAMPLE 10

1,7-dimethyl-5-H-s-triazolo[4,3-a][3,1]benzothiazine

Similarly, 4 g. of 1,4-dihydro-6-methyl-2H-3,1-benzothiazin-2-thione was reacted first with hydrazine and then with acetic acid, following the scheme of Example 8, to form 1.3 g. of 1,7-dimethyl-5H-s-triazolo[4,3-a][3,1]-benzothiazine, m.p. 168° C.

|   | Theoretical | Found |
|---|---|---|
| C | 60.80% | 60.97% |
| H | 5.10 | 5.36 |
| N | 19.34 | 19.58 |

EXAMPLE 11

9-chloro-5H-s-triazolo[4,3-][3,1]benzothiazine

The starting material as 2.2 g. of 8-chloro-1,4-dihydro-2H-3,1-benzothiazin-2-thione, which was reacted as described in Example 8 above to prepare 0.3 g. of 9-chloro-5H-s-triazolo[4,3-a][3,1]benzothiazine, m.p. 203°–204° C.

|   | Theoretical | Found |
|---|---|---|
| C | 48.33% | 48.56% |
| H | 2.70 | 2.97 |
| N | 18.79 | 18.59 |

EXAMPLE 12

7-chloro-1-methyl-5-phenyl-5H-s-triazolo[4,3-a][3,1]benzothiazine

A 1.7 g. portion of 6-chloro-4-phenyl-1,4-dihydro-2H-3,1-benzothiazin-2-thione was reacted with hydrazine and then with acetic acid, as in Example 8, to prepare 0.52 g. of 7-chloro-1-methyl-5-phenyl-5H-s-triazolo[4,3-a]-[3,1]benzothiazine, m.p. 237° C.

|   | Theoretical | Found |
|---|---|---|
| C | 61.24% | 61.22% |
| H | 3.85 | 3.94 |
| N | 13.39 | 13.23 |

The compounds of this invention have been shown in a number of in vivo tests to protect plants from the adverse effects of fungal foliar phytopathogens. The following examples illustrate the tests employed and the results produced by representative compounds.

In most of the tests, each compound was formulated for testing by dissolving or suspending about 3.5 weight percent of it in 50:50 acetone:ethanol containing about 10 g./100 ml. of a nonionic surfactant. The solution was then dispersed in deionized water in a quantity such that the water dispersion contained the various compound concentrations indicated in the specific test methods and the table below. Concentrations are measured in parts per million by weight.

In most of the tests, the compound dispersions were applied to the test plants by spraying them with an air atomizer, using sufficient dispersion to wet the plants thoroughly. Other methods of formulation and application were used in a few tests, as described in the specific test methods which follow.

Untreated, infected controls and untreated, normal controls were included in each test. The results are reported on a 1–5 rating scale where 1 indicates severe disease and 5 indicates complete control of the disease. An empty space in the table below shows that the indicated compound was not tested at the indicated rate. In some cases, more than one test was performed against a given phytopathogen, and the results in such cases are reported as averages. Compounds are identified by the example numbers used above.

TEST 1 late blight of tomato

Four-week-old tomato seedlings were sprayed with aqueous dispersions containing test compounds at compound concentrations indicated in the table below. The following day, the foliage was inoculated with an aqueous suspension of propagules of *Phytophthora infestans*. The inoculum had been reared on infected wheat seed. The plants were held for two days in a moist chamber, and were then transferred to the greenhouse. The plants were observed amd rated for disease control about one week after application of the test compounds.

TEST 2 powdery mildew of bean

The host plants were 10-day-old bean seedlings. After aqueous dispersions containing test compounds at compound concentrations indicated in the table below had been sprayed on the foliage of the beans and allowed to dry, the plants were placed in the greenhouse and inoculated by storing them under other bean plants which were heavily infected with powdery mildew (*Erysiphe polygoni*). After about 10 days, the plants were observed and the results recorded as usual.

TEST 3 bean rust of bean

Pinto bean seeds were planted in sterile greenhouse soil in 2½ inch round plastic pots, and were thinned to one plant per pot. A weel after planting, the pots were treated with test compound dispersions, at concentrations shown below. Each pot received 10 ml. of compound dispersion. The following day, the plants were inoculated with a spore suspension of *Euromyces phaseoli* va. typica which had been grown on pinto beans. The plants were placed in a moist growth chamber for 2 days, and were then transferred to the greenhouse. About 10 days after treatment, the plants were observed and the results recorded.

TEST 4 anthracnose of cucumber

Aqueous dispersions containing test compounds at compound concentrations indicated in the table below were applied to healthy cucumber seedlings grown in sterilized greenhouse soil. The following day, the plants were inoculated with *Colletotrichum lagenarium* conidia as an aqueous suspension. The fungus has been grown on potato dextrose agar in petri dishes. The plants were held in a moist chamber for two days and transferred to the greenhouse, and the disease was observed and rated approximately 12 days after application of the test compounds.

TEST 5 rice blast of rice

The test compound dispersions, at compound concentrations indicated in the table below, were applied to healthy rice seedlings growing thickly in plastic pots. The plants were inoculated on the next day with *Piricularia oryzae* (grown on rice polish agar) and the plants were held in a moist chamber for two days. The plants were then held in the greenhouse for 5–7 days and observed.

TEST 6 helminthosporium leaf spot of wheat

Healthy wheat seed was planted in sterile greenhouse soil. When the seedlings were 4–5 inches tall, they were sprayed with test compound dispersions at compound concentrations indicated in the table below. The day after treatment, the plants were inoculated with a spore suspension of *Helminthosporium sativum* which had been grown on potato dextrose agar. The plants were placed in a moist growth chamber for two days to start disease growth, and were then transferred to the greenhouse. About a week after treatment, the plants were observed and the results were recorded.

TEST 7 botrytis of grape

Sound grape berries were sterilized by immersion in diluted sodium hypochlorite and thoroughly rinsed. The berries were placed on wire screen shelves in compartmented Pyrex plates. The berries were then flamed and sprayed with test chemical dispersions. The following day, the berries were inoculated by spraying 5 ml. of a conidial suspension of *Botrytis cinerea* over each plate containing 12 berries. The inoculum had been grown on frozen lima bean agar. A small amount of water was added to each plate and a cover was sealed over each plate. After 48 hours at 25° C., the berries were observed and disease ratings recorded.

TEST 8 apple scab of apple

Apple seedings at the 4–6 leaf stage were sprayed with aqueous dispersions of the test compounds. The following day, the plants were sprayed with a suspension of fresh conidia of *Venturia inaequalis* obtained from infected apple seedlings kept as a source of inoculum. The plants were held for two days in a 20° C. moist chamber to start disease growth and were then transferred to the greenhouse. About two weeks after application of the compounds, the plants were observed and the results were recorded.

TEST 9 downy mildew of grape

Young expanding grape leaves were detached from healthy vines on the day of the test. Leaves were placed individually in plastic petri dishes, bottom side up, on top of an expanded plastic mat. Water was added to each petri dish, and the petiole of each leaf was wrapped with a water-soaked wad of cotton. Each leaf was sprayed with an aqueous dispersion of the compound to be tested.

After the test compound dispersions had dried, the leaves were inoculated by atomizing a conidial suspension of *Plasmopara viticola* (grown on infected leaf tissue) evenly over the leaf surface. The plates were then covered and were stored in a growth room at about 18° C. and 100% relative humidity where they were exposed to 8 hours a day of artificial light. After about a week of storage, all the leaves were observed and the signs of disease were evaluated.

TEST 10 cercospora leaf spot of sugar beet

Sugar beet seedlings were transplanted into square plastic pots and allowed to grow for three weeks. Aqueous dispersions containing 400 ppm. of the compounds to be tested were sprayed on the leaf surfaces. After the dispersions dried, but within 24 hours, the plants were inoculated with a conidial suspension of *Cercospora beticola* which had been grown on sugar beet leaf decoction agar. After the plants were held in a moist chamber for two days, they were transferred to the greenhouse and observed 2–3 weeks later.

| Compound of Example No. | Appln. Rate ppm. | Late Blight | Powdery Mildew | Bean Rust | Anthracnose | Rice Blast | Helminthosporium | Botrytis | Apple Scab | Downy Mildew | Cercospora |
|---|---|---|---|---|---|---|---|---|---|---|---|
| 2 | 400 | 1 | 1 | 1 | 3 | 3 | | 1 | 3 | 1 | 1 |
| 3 | 400 | 1 | 1 | 1 | .1 | 4 | 1 | 1 | 1 | toxic | 1 |
|   | 100 | | | | | 1 | | | | | |
|   | 25 | | | | | 1 | | | | | |
| 4 | 400 | 1 | 1 | | 4 | 4 | 1 | 1 | | | |
|   | 100 | | | 1 | | | | | | | |
|   | 80 | | | | | 1 | 3 | | | | |
|   | 16 | | | | | 1 | 3 | | | | |
| 5 | 400 | 1 | 1 | | 1 | 3 | 1 | 1 | | | |
|   | 100 | | | 1 | | | | | | | |
| 6 | 400 | 1 | 1 | | 1 | 1 | 1 | 1 | | | |
|   | 100 | | | 5 | | | | | | | |
| 7 | 400 | 1 | 1 | | 2 | 2 | 1 | 1 | | | |
|   | 100 | | | 1 | | | | | | | |
|   | 80 | | | | | 1 | 3 | | | | |
|   | 16 | | | | | 1 | 3 | | | | |
| 8 | 400 | 1 | 1 | 1 | 1 | 1 | 1 | 1 | | | |
|   | 100 | | | 4 | | | | | | | |
| 9 | 400 | | 1 | 1 | 3 | 3 | | 1 | | | |
| 10 | 400 | 1 | 1 | | 1 | 4 | 1 | 1 | 1 | 1 | 1 |
|   | 100 | | | 4 | | 1 | | | | | |
|   | 25 | | | | | 1 | | | | | |
| 11 | 400 | 1 | 1 | 1 | 1 | 4 | 1 | 1 | 1 | 1 | 1 |
|   | 100 | | | | | 4 | | | | | |
|   | 25 | | | | | 1 | | | | | |
| 12 | 400 | | 1 | 1 | 3 | 2 | | 1 | | | |

The test data reported above show that the compounds of this invention are useful for the protection of plants from the adverse effects of a variety of fungal foliar phytopathogens. Accordingly, an important aspect of the invention is a new method of reducing the adverse effects of fungal foliar phytopathogens which comprises contacting the phytopathogens with an effective phytopathogen-inhibiting amount of one of the compounds described above. The method is carried out by applying a compound of the invention to the plants to be protected. The compound may either be applied to the foliage, or to the soil around the plant, whence it is picked up by the root system and distributed to the foliage through the plant's vascular system.

Practice of the method does not necessarily kill the phytopathogens. As the data above show, application of a phytopathogen-inhibiting amount of a compound reduces the adverse effects of the disease, even though only a part of the phytopathogen population may be killed by the compound. The term "phytopathogen-inhibiting amount" is used here to describe an amount which is sufficient to reduce the adverse effects of a phytopathogen. The term "reducing the adverse effects" refers to weakening the pathogen sufficiently that its reproduction rate and its vigor are decreased, with the result that the express signs of the disease, and the concomitant injury to the host plant, are decreased as compared with phytopathogens growing on untreated plants.

As is usual in the plant protection art, best results are obtained by applying the compound several times during the growing season at intervals of from one to a few weeks, depending on the weather and the severity of the disease.

The methods of formulating the compounds and preparing dispersions of the formulations, and the methods of applying dispersions of the compounds to the plants to be protected, are entirely conventional in the plant protection art. Some explanation of the methods of application will be given merely to assure that those skilled in the art can carry out the invention without undue experimentation.

It is usual in describing foliar applications of plant protectants to measure the application rate by the concentration of the dispersion in which it is applied. The application rate is measured in this way because it is customary to apply a sufficient amount of the dispersion to cover the foliage with a thin film. The amount of dispersion applied is thus dependent on the foliar area of the plants being treated, and the quantity of plants protecting compound is dependent upon its concentration in the dispersion. In general, compound concentrations in the range of from about 50 to about 1500 parts of compound per million parts by weight of dispersion are used in the practice of this invention.

On the other hand, when the compounds are applied to the soil, it is usual to measure them by the weight of compound applied per unit area. In general, from about 1 to about 25 kilograms of compound per hectare are used in the practice of this invention. Of course, from time to time, higher or lower application rates will be useful, depending on the severity of the infection and the characteristics of the specific compound in use. The named ranges, however, enclose the usual optimum application rates of the compounds.

The dispersions in which the compounds are applied are most often aqueous suspensions are emulsions prepared from concentrated formulations of the compounds. Such water-suspendible or emulsifiable formulations are either solids usually known as wettable powders or liquids usually known as emulisifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as terpenic solvents including rosin derivatives, and complex alcohols such as 2-ethoxyethanol. Suitable emulsifiers for emulsifiable concentrates are chosen from the same types of surfactants used for wettable powders.

Adjuvants are frequently used to improve the ability of the aqueous dispersion to coat and adhere to foliage. Such adjuvants as gums, emulsified polybutenes, cationic surfactants and lignin derivatives can often increase the potency of the method in a specific use.

Less frequently, the compounds are applied to foliage in the form of dusts. Agricultural chemical dusts typically comprise the compound in a finely powdered form, dispersed in a powdered inert carrier. Most often, the carrier is a powdered clay, such as pyrophyllite, bentonite, a volcanic deposit, or montmorillonite. Dusts are usually prepared to contain concentrations of the compound at the highest part of the concentration range, such as 1500 ppm., and may contain even more active ingredient.

Dispersions of the compounds are applied in the usual manners. Low-pressure sprayers, high-pressure sprayers and low-volume air blast equipment are all effective for the application of water-dispersed compounds of the invention. Dust dispersions are readily applied by means of the usual equipment which blows the dust into intimate contact with the foliage.

The compounds can also conveniently be applied to the soil in the form of granular formulations. Such formulations are prepared by dispersing the compound on an inert carrier of controlled granular character and are frequently used in agricultural chemistry. Most often, the carrier is a coarsely ground clay, such as attapulgite of kaolin clay, having a particle size in the range of from 0.5 to 3 mm. Such granular formulations are easily applied to the soil with applicators which are specially designed to apply accurately controlled amounts of the granular products to the soil.

I claim:
1. A compound of the formula

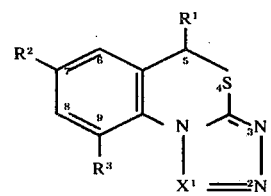

wherein
X represents

R represents hydrogen or $C_1$–$C_4$ alkyl;
$R^1$ represents hydrogen or phenyl;
$R^2$ and $R^3$ independently represent hydrogen, $C_1$–$C_3$ alkyl, chloro or bromo;
provided that at least one of $R^2$ and $R^3$ represents hydrogen; that $R^3$ represents hydrogen when X represents

and R represents $C_1$–$C_4$ alkyl and that $R^2$ does not represent $C_1$–$C_3$ alkyl when X represents

2. The compound of claim 1 which is 9-chloro-5H-tetrazolo[1,5-a][3,1]benzothiazine.

3. The compound of claim 1 which is 5H-tetrazolobenzothiazine.

4. The compound of claim 1 which is 9-methyl-5H-s-triazolo[4,3-a][3,1]benzothiazine.

5. The compound of claim 1 which is 1,7-dimethyl-5H-s-triazolo-[4,3-a][3,1]benzothiazine.

6. The compound of claim 1 which is 9-chloro-5H-s-triazolo[4,3-a][3,1]benzothiazine.

* * * * *

UNITED STATES PATENT AND TRADEMARK OFFICE
CERTIFICATE OF CORRECTION

PATENT NO. : 4,001,227
DATED : January 4, 1977
INVENTOR(S) : Barry A. Dreikorn

It is certified that error appears in the above–identified patent and that said Letters Patent are hereby corrected as shown below:

Claim 3 should read --

3. The compound of Claim 1 which is 5H-tetrazolo-[1,5-a][3,1]benzothiazine.

Signed and Sealed this

Nineteenth Day of April 1977

[SEAL]

Attest:

RUTH C. MASON
*Attesting Officer*

C. MARSHALL DANN
*Commissioner of Patents and Trademarks*